United States Patent
Allegretti et al.

(10) Patent No.: US 6,916,926 B2
(45) Date of Patent: *Jul. 12, 2005

(54) PROCESS FOR THE PREPARATION OF (±) 1-3-DIOXOLANES AND THE OPTICAL RESOLUTION THEREOF

(75) Inventors: Marcello Allegretti, L'Aquila (IT); Maria Candida Cesta, L'Aquila (IT); Roberto Curti, L'Aquila (IT); Luca Nicolini, L'Aquila (IT)

(73) Assignee: DOMPE S.p.A., L'Aquila (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/312,290
(22) PCT Filed: Jul. 18, 2001
(86) PCT No.: PCT/EP01/08305
  § 371 (c)(1),
  (2), (4) Date: May 13, 2003
(87) PCT Pub. No.: WO02/10150
  PCT Pub. Date: Feb. 7, 2002

(65) Prior Publication Data
US 2003/0176446 A1 Sep. 18, 2003

(30) Foreign Application Priority Data
Jul. 28, 2000 (IT) .......................... MI00A1735

(51) Int. Cl.$^7$ .................. C07D 405/06; C07D 295/088
(52) U.S. Cl. ................. 544/230; 544/374; 544/392
(58) Field of Search .................. 544/230, 374, 544/392

(56) References Cited

U.S. PATENT DOCUMENTS

| | | |
|---|---|---|
| 4,372,958 A | 2/1983 | Pestellini et al. |
| 4,669,911 A | 6/1987 | Lundgren et al. |
| 4,699,911 A | 10/1987 | Borsa et al. |
| 2004/0038989 A1 * | 2/2004 | Allegretti et al. ........ 514/254.1 |

FOREIGN PATENT DOCUMENTS

WO  WO 93/16056 A  8/1993

* cited by examiner

Primary Examiner—Emily Bernhardt
(74) Attorney, Agent, or Firm—Birch, Stewart Kolasch & Birch, LLP

(57) ABSTRACT

(±) 3-(4-Phenyl-1-piperazinyl)-1,2-propanediol cyclic acetals, a process for the optical resolution thereof and their use as intermediates for the preparation of (−) 3-(4-phenyl-1-piperazinyl)-1,2-propanediol (levodropropizine) and salts thereof are described herein.

12 Claims, No Drawings

PROCESS FOR THE PREPARATION OF (±) 1-3-DIOXOLANES AND THE OPTICAL RESOLUTION THEREOF

This application is the national phase under 35 U.S.C. § 371 of PCT International Application No. PCT/EP01/08305 which has an International filing date of Jul. 18, 2001, which designated the United States of America.

The present invention relates to (±) 3-(4-phenyl-1-piperazinyl)-1,2-propanediol cyclic acetals, a process for their optical resolution and the use thereof as intermediates for the preparation of (−)3-(4-phenyl-1-piperazinyl)-1,2-propanediol (levodropropizine) and the salts thereof.

More precisely, the invention relates to (±) 2,2-substituted-1,3-dioxolanes of formula (1):

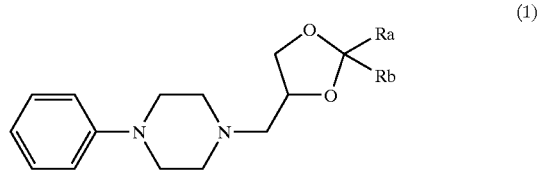

(1)

wherein:
each of Ra and Rb, which can be the same or different, is hydrogen, $C_1$–$C_6$-alkyl, phenyl, or
Ra and Rb taken together with the C atom they are linked to, form an optionally substituted 4- to 7-membered carbocyclic ring.

Advantageously, in the compounds of the invention of formula (1), Ra and Rb are alkyl groups containing less than 6 C atoms. Ra and Rb are preferably the same; more preferably, Ra and Rb are methyl or ethyl or, together with the C atom they are linked to, form a ring containing 5 to 6 carbon atoms.

The invention also relates to the enantiomerically pure monobasic salts of the 2,2-substituted-1,3-dioxolanes of formula (1) with pharmaceutically acceptable chiral acids such as L-malic, D- and L-tartaric, D- and L-mandelic, L- and D-camphorsulfonic acids.

Examples of particularly preferred compounds of the invention are:

(±) 1,2-cyclopentylidene-3-(4-phenyl-piperazin-1-yl)-propane-1,2-diol;
(±) 1,2-cyclohexyliden-3-(4-phenylpiperazin-1-yl)-propane-1,2-diol;
(±) 1,2-(2-propylidene)-3-(4-phenyl-piperazin-1-yl)-propane-1,2-diol;
(±) 1,2-(3-pentyliden)-3-(4-phenyl-piperazin-1-yl)-propane-1,2-diol;
S(−)-1,2-cyclohexyliden-3-(4-phenylpiperazin-1-yl)-propane-1,2-diol L-tartrate;
S(−)-1,2-cyclopentylidene-3-(4-phenylpiperazin-1-yl)-propane-1,2-diol L-tartrate.

The compounds of the invention of formula (1) are prepared by reacting phenylpiperazine with a (±)1,2-glyceryl-dioxolane of formula (2):

(2)

wherein X is selected from the group consisting of Cl, Br, I and a suitable sulfonic ester (R—$SO_3$—), R being selected from the group consisting of $C_1$–$C_3$-alkyl (preferably methyl), trifluoromethyl, phenyl, p-tolyl and p-methoxy phenyl.

Dioxolanes of formula (2) are known compounds and/or can be prepared according to known methods.

The sulfonic esters of formula (2) (X=R—$SO_3$—) are prepared by esterification with an anhydride or with an alkyl- and/or aryl-sulfonic acid chloride of formula (3)

R—$SO_3$H     (3)

of a (±) 2,2-substituted-1,3-dioxolane-4-methanol of formula (4):

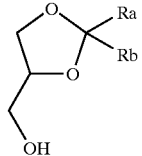

(4)

wherein Ra and Rb have the meanings defined above.

Compounds of formula (4) are known compounds. Racemates of formula (4) are, in fact, used as substrates for fermentative resolution processes [U.S. Pat. No. 5,190,867 (Mar. 2, 1993)]. The preparation of dl-isopropylideneglycerol (Merck 12.5232; Beil 19.65) starting from glycerol is described in Org. Synth. Coll. Vol III.

The 4-halomethyl-dioxolanes of formula (2) wherein X is Cl, Br or I can be prepared starting from the corresponding sulfonates of formula (2) (X=$RSO_3$— wherein R is as defined above) by reaction with an alkali or alkaline-earth halide in an inert solvent, selected from the group consisting of acetone, methyl ethyl ketone, tetrahydrofuran, dioxane, dimethylsulfoxide, acetonitrile, a $C_1$–$C_4$-alcohol and mixtures thereof. A preferred method for the synthesis of said compounds comprises the dioxolanation of the corresponding 3-halo-1,2-propanediols, as disclosed in EP 0930311 (Jul. 21, 1999). Particularly preferred is 3-chloro-propane-1,2-diol; preferred acetalyzing agents are formaldehyde, acetaldehyde and benzaldehyde, acetone, diethyl ketone, benzophenone, cyclohexanone, the acetals and/or enol ethers thereof, such as 2,2-dimethoxypropane, 2,2-dimethoxyethane, 2-methoxy-propene.

Alternatively, dioxolanes of formula (2) (X=Cl or Br) can also be obtained by acetalyzation of epichlorohydrins or epibromohydrins with a cycloalkanone according to the processes described for the preparation of (+)2-chloromethyl-1,4-dioxaspiro[4,5]-decane in FR 1522153 or by Blicke F F et al., J.A.C.S, 74, 1735 (1972) and ibidem, 76, 1226 (1954).

The alkylation reaction of phenylpiperazine with a 1,2-glyceryl-dioxolane of formula (2) is performed using reaction conditions conventionally used for the conversion of a secondary amine to a tertiary amine, using for each mol of the alkylating agent of formula (2) at least one mol or a slight molar excess of phenylpiperazine in the presence of at least one mol of a counterbase. The counterbase is used in at least equimolar amounts with respect to the alkylating agent of formula (2), and is selected from the group consisting of finely divided inorganic bases such as alkali or alkaline-earth (Na, K, Mg, Ca) carbonates or bicarbonates or Ca or Mg oxides, or tertiary amines as triethylamine, dimethyl or diethylaniline, aromatic amines as pyridine, picoline and collidine and, if desired, the phenylpiperazine itself which may be subsequently recycled to a subsequent production cycle.

The alkylation reaction can be performed in the hot, optionally in the presence of inert solvents such as toluene or xylene which, when operating under reflux of the solvent, will advantageously reduce the reaction times.

After completion of the alkylation reaction, any insolubles are filtered or centrifuged off, then the organic phases are repeatedly washed with water to easily remove the impurities and side-products, and the solvent is distilled off to obtain in high yields a residue consisting of a substantially pure 1,3-dioxolane of the invention of formula (1), which is recovered either by direct crystallization or after salification with a molar equivalent of a carboxylic acid.

Compounds (1) and the salts thereof are suprisingly easy to crystallize from the usual solvents: the process of the invention therefore minimizes any risks of contaminations due to the presence of glycidols and/or epihalohydrins traces as potential impurities.

The monobasic salts of the compounds of formula (1) are obtained by using conventional methods such as salification with equimolecular amounts of the desired acid in a suitable solvent and subsequent crystallization of the resulting salt.

It has been found that the salification of compounds (1) with chiral acids, particularly with L-tartaric acid, is an efficient optical resolution method to recover the S-enantiomers of compounds (1) in high yields.

Said (S)(-) enantiomers and the salts thereof are useful as antitussive agents or as intermediates for the synthesis of (-) 3-(4-phenyl-1-piperazinyl)-1,2-propanediol (levodropropizine), by hot hydrolysis of aqueous solutions of the (-)1,3-dioxolanes of formula (1) catalyzed by a molar excess of a diluted aqueous solution of a mineral acid such as hydrochloric acid, or of a carboxylic acid such as acetic, malonic or citric acids.

The following examples further illustrate the invention.

EXAMPLE 1

A solution of 11.98 g of (±) 2,3-O-(3-pentylidene)-glycerol tosylate in n-butanol (70 mL) is added under strong stirring with 4.5 g of finely divided sodium carbonate, then with 6 ml of phenylpiperazine. The mixture is refluxed under stirring and reacted at this temperature for 20 h. Butanol is then evaporated off under reduced pressure, the residue is taken up with water and repeatedly extracted with ethyl acetate. The combined organic phases are dried and filtered, then the solvent is evaporated off under vacuum and the resulting residue is crystallized from aqueous methanol to obtain 8.95 g of (±) 1,2-(3-pentyliden)-3-(4-phenyl-piperazin-1-yl)-propane-1,2-diol, also named 4-phenylpiperazine, 1-(2,2-diethyl-1,3-dioxolan-4-yl-methyl).

EXAMPLE 2

Following the procedure described in Example 1, using (±) 2,3-O-(2-propylidene)-glycerol tosylate, (±) 1,2-(2-propylidene)-3-(4-phenyl-piperazin-1-yl)-propane-1,2-diol, also named 4-phenylpiperazine, 1-(2,2-dimethyl-1,3-diossolan-4-yl-methyl), is obtained.

EXAMPLE 3

A solution of 3.28 g of (±) 1,4-dioxaspiro-[4.5]decane-2-methyl chloride in toluene (16 mL) is added under inert gas atmosphere with 5.45 ml of phenylpiperazine. The mixture is then refluxed to complete the reaction (approximately 8 hours). The reaction mixture is cooled to about 50° C., added with 10 ml of water and kept under strong stirring for at least 10 minutes. The phases are separated, and the organic phase is repeatedly washed with water. The solvent is evaporated off to obtain a thick oil which is dissolved in hot isopropanol (15 mL). The resulting solution is slowly cooled to separate (±) 1,2-cyclohexyliden-3-(4-phenylpiperazin-1-yl)propane-1,2-diol as a crystalline solid, m.p. 58–61° C.

$^1$H NMR δ 7.26 (t, 2H, J=7.4 Hz); δ 6.95 (d, 2H, J=8.9 Hz); δ 6.85 (t, 1H), J=7.28 Hz); δ 4.3 (m, 1H, J=6.1 Hz); δ 4.1 (dd, 1H, $J_1$=8.0 Hz, $J_2$=6.1 Hz); δ 3.65 (dd, 1H, $J_1$=8.0, $J_2$=7.1 Hz); δ 3.2 (t, 4H, J=5.05 Hz); δ 2.9÷2.55 (m, 6H); δ 1.7÷1.3 (m, 10H).

EXAMPLE 4

Following the procedure described in Examples 1 and 3, by reacting a 1.3-dioxolane selected from the group consisting of:

- (±) 1,4-dioxaspiro[4.4]nonane-2-methanol, mesylate;
- (±) 1,4-dioxaspiro[4.4]nonane-2-methyl chloride;
- (±) 1,4-dioxaspiro[4.5]decane-2-methanol, trifluoromethanesulfonate;
- (±) 1,4-dioxaspiro-[4.5]decane-2-methanol, mesylate;
- (±) 1,3-dioxolane-4-chloromethyl-2,2-dimethyl;
- (±) 1,3-dioxolane-4-bromo-methyl-2,2-dimethyl;

with phenylpiperazine, the following compounds were obtained:

- (±) 1,2-cyclopentylidene-3-(4-phenyl-piperazin-1-yl)-propane-1,2-diol;
- (±) 1,2-cyclohexylidene-3-(4-phenyl-piperazin-1-yl)propane-1,2-diol;
- (±) 1,2-(2-propylidene)-3-(4-phenyl-piperazin-1-yl)-propane-1,2-diol.

EXAMPLE 5

3 g of L-tartaric acid are added under stirring to a solution of (±) 1,2-cyclohexylidene-3-(4-phenyl-piperazin-1-yl) propane-1,2-diol (6.32 g) in absolute ethanol (70 ml). The mixture is stirred until complete dissolution, then cooled to 5–8° C. 4.05 g of a crystalline solid are obtained, which is recrystallized from absolute ethanol to yield 3.82 g of S(-)-1,2-cyclohexylidene-3-(4-phenyl-piperazin-1-yl) propane-1,2-diol L-tartrate m.p. 131–132° C., $[\alpha]_D$=-9.6° (c=1%; meoh);

$^1$H NMR δ 7.5 (dd, 2H, $J_1$=8.7 $J_2$=7.3); δ 7.2 (m, 3H); δ 4.8 (m, 1H); δ 4.4 (s, 2H); δ 4.35 (dd, 1H, $J_1$=8.9 Hz $J_2$=6.7 Hz); δ 3.86 (dd, 1H, $J_1$=8.9 Hz $J_2$=5.8 Hz); δ 3.6–3.4 (m, 10H); δ 1.8–1.48 (m, 10H).

EXAMPLE 6

A solution of 2.4 g of S(-)-1,2-cyclohexylidene-3-(4-phenyl-piperazin-1-yl)propane-1,2-diol L-tartrate in water is alkalinized (pH=8) by addition of 2N NaOH, then exhaustively extracted with ethyl acetate. The combined organic phases are washed with a 10% monobasic sodium phosphate solution, dried over sodium sulfate and evaporated to dryness, then crystallized from isopropanol to obtain 1.5 g of S(-)-1,2-cyclohexylidene-3-(4-phenyl-piperazin-1-yl) propane-1,2-diol, m.p. 63–64° C., $[\alpha]_D$=-7.8° (1% MeOH).

$^1$H NMR δ7.26 (t, 2H, J=7.4 Hz); δ 6.95 (d, 2H, J=8.9 Hz); δ 6.85 (t, 1H, J=7.28 Hz); δ 4.3 (m, 1H, J=6.1 Hz); δ 4.1 (dd, 1H, $J_1$=8.0 Hz, $J_2$=6.1 Hz); δ 3.65 (dd, 1H, $J_1$=8.0, $J_2$=7.1 Hz); δ 3.2 (t, 4H, J=5.05 Hz); δ 2.9÷2.55 (m, 6H); δ 1.7÷1.3 (m, 10H).

EXAMPLE 7

By salification of a 1,3-dioxolane prepared according to the processes of Examples 1–4 with L-tartaric acid and fractional recrystallization of the resulting salts, the following compounds were prepared:

S(-)-1,2-cyclopentylidene-3-(4-phenyl-piperazin-1-yl)-propane-1,2-diol, L-tartrate;

S(-)-1,2-(2-propylidene)-3-(4-phenyl-piperazin-1-yl)-propane-1,2-diol, L-tartrate;

S(−)-1,2-(3-pentylidene)-3-(4-phenyl-piperazin-1-yl)-propane-1,2-diol, L-tartrate;

which where subsequently neutralized according to the process of Example 6, to obtain the corresponding free bases.

EXAMPLE 8

A suspension of 2.8 g of S(−)-1,2-cyclopentylidene-3-(4-phenyl-piperazin-1-yl)-propane-1,2-diol in 70 ml of aqueous acetic acid (10% w/v) is refluxed for 2 h, then vapor is bubbled therein to distil off cyclopentanone, which is separated. The aqueous phase is neutralized to pH 7.5 by addition of a 10% NaOH solution, then cooled to 5–10° C., to obtain 1.97 g of (−) 3-(4-phenyl-piperazin-1-yl)-propanediol m.p. 102–103° C., $[\alpha]_D = -23.5°$ (2.8% $CH_2Cl_2$).

EXAMPLE 9

Alternatively, 0.35 molar equivalents of one of the 1,3-dioxolane derivatives described in Examples 6 and 7, S(−) 1,2-(2-propylidene)-3-(4-phenyl-piperazin-1-yl)-propane-1,2-diol; S(−) 1,2-cyclopentylidene)-3-(4-phenyl-piperazin-1-yl)-propane-1,2-diol; S(−)-1,2-cyclohexylidene-3-(4-phenyl-piperazin-1-yl)propane-1,2-diol; are added in portions to a 36% hydrochloric acid solution (36 mL) in 45 ml of water under stirring; the suspension is heated to 80° C. to obtain a clear solution, which is kept at this temperature for a further 30 minutes, then cooled to 20–25° C. and the aqueous phase is repeatedly is extracted with dichloromethane (3×15 ml), then added with n-butanol (0.5 l). The diphasic mixture is refluxed to distil the water n-butanol azeotrope, recovering about 300 ml of distillate, then cooled to promote the crystallization of (−)3-(4-phenyl-piperazin-1-yl)-propanediol hydrochloride (85 g).

A solution of the hydrochloride in 125 ml of water is decolorized by heating at 50° C. with active charcoal (2.2 g) for 15 minutes, filtered then neutralized by addition of an ammonium hydroxide aqueous solution (30% w/w). After briefly heating to 50° C., crystallization is started by addition of (−) 3-(4-phenyl-piperazin-1-yl)-propanediol crystals. The suspension is left to spontaneously cool, then kept for 2 hours at +2–+4° C., finally filtered to yield 70–72 g of (−) 3-(4-phenyl-piperazin-1-yl)-1,2-propanediol.

What is claimed is:

1. A compound of formula (1)

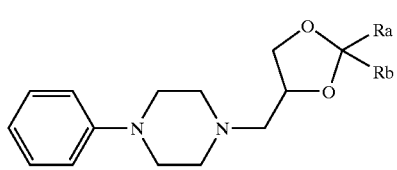

(1)

wherein:
each of Ra and Rb, which can be the same or different, is hydrogen, $C_1$–$C_6$-alkyl, phenyl, or Ra and Rb taken together with the C atom they are linked to, form a 4- to 7-membered carbocyclic ring, or a salt thereof.

2. The compound as claimed in claim 1, wherein Ra and Rb are the same.

3. The compound as claimed in claim 1, wherein each of Ra and Rb is methyl or ethyl.

4. A compound selected from the group consisting of:
(±) 1,2-cyclopentylidene-3-(4-phenyl-piperazin-1yl)-propane-1,2-diol;
(±) 1,2-cyclohexylidene-3-(4-phenyl-piperazin-1-yl)-propane-1,2-diol;
(±) 1,2-(2-propylidene)-3-(4-phenyl-piperazin-1-yl)-propane-1,2-diol;
(±) 1,2-(3-pentylidene)-3-(4-phenyl-piperazin-1-yl)-propane-1,2-diol;
S(−)-1,2-cyclohexylidene-3-(4-phenyl-piperazin-1-yl)-propane-1,2-diol L-tartrate; and
S(−)-1,2-cyclopentylidene-3-(4-phenyl-piperazirin-1-yl)-propane-1,2-diol L-tartrate.

5. A process for the preparation of a compound of formula (1):

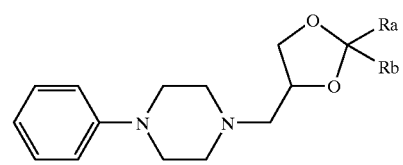

(1)

wherein each of Ra and Rb, which can be the same or different, is hydrogen, $C_1$–$C_6$-alkyl, phenyl, or Ra and Rb taken together with the C atom they are linked to, form a 4- to 7-membered carbocyclic ring, and salts thereof, said method comprising the steps of reacting phenylpiperazine with a (±) 1,2-glyceryl-dioxolane of formula (2):

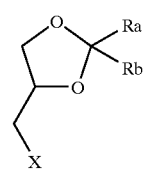

(2)

wherein X is selected from the group consisting of Cl, Br, I and a suitable sulfonic ester (R—$SO_3$—), R is selected from the group consisting of $C_1$–$C_3$-alkyl, trifluoromethyl, phenyl, p-tolyl and p-methoxy phenyl, and Ra and Rb have the same meanings as defined above; and recovering the compound of formula (1).

6. The process as claimed in claim 5, wherein the reaction is carried out in the presence of a base, using toluene or xylene as solvents.

7. The process according to claim 5, wherein R of the suitable ester of X in formula (2) is methyl.

8. The process for the optical resolution of the compounds of any one of claims 1–4 by salification with L-tartaric acid.

9. A process for the synthesis of corresponding (S) enantiomers of the compounds of any one of claims 1–4 comprising the step of salificating said compounds with a chiral acid.

10. A process for the synthesis of (−) 3-(4-phenyl-1-piperazinyl)-1,2-propanediol wherein the tartaric-acid salts of a compound of formula (1)

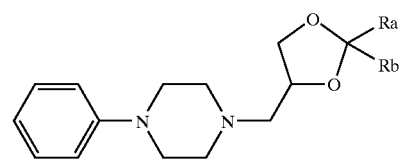

(1)

wherein:

each of Ra and Rb, which can be the same or different, is hydrogen, $C_1$–$C_6$-alkyl, phenyl, or Ra and Rb taken together with the C atom they are linked to, form a 4- to 7-membered carbocyclic ring, and salts thereof, are optically resolved to recover the S (−)-enantiomers which are then subjected to hot hydrolysis catalyzed by a molar excess of a diluted aqueous solution of a mineral acid.

11. The process according to claim 10, wherein the mineral acid is hydrochloric acid, acetic acid, malonic acid or citric acid.

12. A method for preparing (−) 3-(4-phenyl-1-piperazinyl)-1,2-propanediol comprising the steps of catalyzing the compounds of any one of claims 1–4 with a molar excess of a diluted aqueous solution of a mineral acid, and hot hydrolyzing said aqueous solution.

\* \* \* \* \*